US010188698B2

(12) United States Patent
Qi

(10) Patent No.: US 10,188,698 B2
(45) Date of Patent: *Jan. 29, 2019

(54) SAPOSIN C-DOPS: A NOVEL ANTI-TUMOR AGENT

(71) Applicant: Children's Hospital Medical Center, Cincinnati, OH (US)

(72) Inventor: Xiaoyang Qi, Loveland, OH (US)

(73) Assignee: CHILDREN'S HOSPITAL MEDICAL CENTER

(*) Notice: Subject to any disclaimer, the term of this patent is extended or adjusted under 35 U.S.C. 154(b) by 0 days.

This patent is subject to a terminal disclaimer.

(21) Appl. No.: 14/566,501

(22) Filed: Dec. 10, 2014

(65) Prior Publication Data

US 2015/0125497 A1 May 7, 2015

Related U.S. Application Data

(60) Division of application No. 12/332,809, filed on Dec. 11, 2008, now Pat. No. 8,937,156, which is a continuation of application No. 10/801,517, filed on Mar. 16, 2004, now Pat. No. 7,834,147.

(60) Provisional application No. 60/466,166, filed on Apr. 28, 2003.

(51) Int. Cl.
*A61K 38/17* (2006.01)
*A61K 9/48* (2006.01)
*A61K 31/685* (2006.01)
*A61K 9/51* (2006.01)

(52) U.S. Cl.
CPC ............ *A61K 38/17* (2013.01); *A61K 9/4816* (2013.01); *A61K 31/685* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,588,580 A | 5/1986 | Gale et al. | |
| 4,788,062 A | 11/1988 | Gale et al. | |
| 4,816,258 A | 3/1989 | Nedberge et al. | |
| 4,873,192 A | 10/1989 | Kunkel et al. | |
| 4,904,475 A | 2/1990 | Gale et al. | |
| 4,927,408 A | 5/1990 | Haak et al. | |
| 4,940,587 A | 7/1990 | Jenkins et al. | |
| 5,605,793 A | 2/1997 | Stemmer | |
| 5,700,909 A | 12/1997 | O'Brien | |
| 5,707,649 A * | 1/1998 | Inokuchi | A61K 31/5375 424/422 |
| 5,837,458 A | 11/1998 | Minshull et al. | |
| 6,872,406 B2 * | 3/2005 | Qi | C07K 14/475 424/450 |
| 7,834,147 B2 * | 11/2010 | Qi | A61K 31/685 424/450 |
| 9,271,932 B2 * | 3/2016 | Qi | A61K 9/0014 |
| 9,274,932 B2 | 3/2016 | Qi | |
| 2001/0044131 A1 | 11/2001 | Meyers | |
| 2002/0081698 A1 | 6/2002 | Glucksmann | |
| 2002/0099001 A1 | 7/2002 | Habberfield | |
| 2002/0177551 A1 | 11/2002 | Terman | |
| 2003/0095999 A1 | 5/2003 | Qi | |
| 2004/0120961 A1 | 6/2004 | Koochekpour et al. | |
| 2005/0100591 A1 | 5/2005 | Qi | |
| 2010/0311844 A1 | 12/2010 | Qi et al. | |

FOREIGN PATENT DOCUMENTS

| | | | |
|---|---|---|---|
| WO | WO 9104014 A1 * | 4/1991 | ........... A61K 9/1271 |
| WO | 94/04188 A1 | 3/1994 | |
| WO | 9503821 A1 | 2/1995 | |
| WO | 9833482 A1 | 8/1998 | |
| WO | 98/42746 A2 | 10/1998 | |
| WO | 00/02902 A1 | 1/2000 | |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Skolnick et al., From genes to protein structure an function: novel applications of computational approaches in the genomic era, Trends in Biotech. 18: 34-39, 2000.*
Qi et al, Functional Human Saposins Expressed in *Escherichia coli*, J. Biol. Chem., Jul. 17, 1999, 269(24):16746-16743, Amer. Soc. Biochem. Mol. Biol., Inc., U.S.A.
Vaccaro et al, Saposin C induces pH-dependent destablization and fusion of phosphatidylserine-containing vesicles, FEBS Letters, 1994, 349:181-186, U.S.A.
Qi et al, Differential Membrane Interactions of Saposins A and C, J. Biol. Chem., Jul. 20, 2001, 276 (29):27010-27017, Amer. Soc. Biochem. Mol. Biol., Inc., U.S.A.
Luchette et al, Morphology of fast-tumbling bicelles: a small angle neutron scattering and NMR study, Biochim Biophys Acta, Aug. 2001, 1513(2):83-94, Elsevier Science B.V.
Nieh et al, SANS Study on the Effect of Lanthanide Ions and Charged Lipids on the Morphology of Phospholipid Mixtures, Biophysical J., 2002, 82:2487-2498, Biophy. Soc., USA.
Wang et al, Phospholipid vesicle fusion induced by saposin C, ABB, 2003, 415:43-53, Elsevier Science, USA.

(Continued)

*Primary Examiner* — Hong Sang
(74) *Attorney, Agent, or Firm* — Alicia M. Passerin, Esq.; Leech Tishman Fuscaldo & Lampl

(57) ABSTRACT

Compositions and methods for treating subjects with disorders characterized by hyper-proliferating cells such as tumors and cancers are provided. The compositions comprise agents that are combinations of saposin C (or prosaposin-related polypeptides) and phospholips (or inner leaflet components). This anti-tumor agent is administered in the methods of the invention according to a dosing regimen. Administering an agent of the invention results in a positive therapeutic response in a subject with a tumor.

19 Claims, 5 Drawing Sheets

Specification includes a Sequence Listing.

(56) References Cited

OTHER PUBLICATIONS

Nieh et al, Concentration-Independent Spontaneously Forming Biomimetric Vesicles, Phys. rev. Lett., 2003, 91(15)158105-1/4, Amer. Phys. Society, USA.
Nucleotide Sequence: BC001503.
Alam et al., N. Engl. J. Med., vol. 344(13) (2001) pp. 975-983.
Altschul et al., J. Mol. Biol., vol. 215 (1990) p. 403.
Altschul et al., Nucleic Acids Res., vol. 25 (1997) pp. 3389-3402.
Ausubel et al., Current Protocols in Molecular Biology, John Wiley & Sons, New York (2002).
Barry (ed.), Dermatological Formulations: Percutaneous Absorption, Marcel Dekker, Inc. (1983).
Bevers et al., Lupus Suppl, vol. 2 (1998) pp. S126-S131.
Boni et al., Neuroendocrinology Letters, vol. 2382 (2002) pp. 48-51.
Chang et al., Anal. Biochem., vol. 91 (1978) pp. 13-31.
Cheng et al., Arch. Biochem. & Biophys., vol. 415 (2003) pp. 45-53.
Corpet et al., Nucleic Acids Res., vol. 15 (1997) pp. 436-438.
Crameri et al., Nature Biotech., vol. 15 (1997) pp. 436-438.
Crameri et al., Nature, vol. 391 (1998) pp. 288-291.
Dayhoff et al., Atlas of Protein Sequence and Structure, Natl. Biomed. Res. Foundation, Washington D.C. (1978).
Fu et al., J. Mol. Neurosci, vol. 5 (1994) pp. 59-67.
Fujibayashi et al., Am. J. Hum. Genet., vol. 37 (1985) pp. 741-748.
Furst, Biochim. Biophys. Acta, vol. 1126 (1992) pp. 1-16.
Grabowski et al., Critical Review Biochem. Mol. Biol., vol. 25 (1990) pp. 385-414.
Hadgraft and Guy (eds.), "Transdermal Drug Delivery: Developmental Issues and Research Initiatives" Marcel Dekker, Inc. (1989).
Higgins et al., Gene, vol. 73 (1988) pp. 237-244.
Higgins et al., CABIO, vol. 5 (1989) pp. 151-153.
Huang et al., CABIOS, vol. 8 (1992) pp. 155-165.
Karlin et al., Proc. Natl Acad. Sci., vol. 87, USA (1990) pp. 2264-2268.
Kishimoto et al., J. Lipid Res., vol. 33 (1992) p0p. 1255-1267.
Kubo et al., J. Med. Invest., vol. 49 (2002) pp. 111-117.
Kunkel, Proc. Natl. Acad. ScI. USA, vol. .82 (1985) pp. 488-492.
Kunkel et al., Methods in Enzymol., vol. 154 (1987) pp. 367-382.
Kydonieus & Berner (eds.), Transdermal Delivery of Drugs, vols. 1-3, CRC Press (1987).
Mackay et al., Adv. Drug Del. Rev., vol. 7 (1991) pp. 313-338.
Myers et al., CABIOS, vol. 4 (1988) pp. 11-17.
Moore, J. Mol. Biol., vol. 272 (1997) pp. 336-347.
Nakano et al., J. Biochem., vol. 105 (1989) pp. 152-154.
Needleman et al., J. Mol. Biol., vol. 48 (1970) pp. 443-453.
O'Brien et al., Science, vol. 241 (1988) pp. 1098-1101.
Pearson et al., Proc. Natl. Acad. Sci., vol. 85 (1988) pp. 2444-2448.
Physicians Desk Reference (1992 Edition).
Qi et al., Biochemistry. vol. 37 (1998) pp. 11544-11554.
Qi et al., J. Biol. Chem, vol. 275 (2001) pp. 27010-27017.
Reiner et al., J. Mol. Neurosci, vol. 1 (1989) pp. 225-233.
Robinson and Lee (eds.), Controlled Drug Delivery: Fundamentals and Applications, Marcel Dekker, In. (1987).
Rorman et al., Genomics, vol. 5 (1989) pp. 486-492.
Smith et al., Adv. Appl. Math., vol. 2, (1981) p. 482-489.
Stemmer, Proc. Natl. Acad. Sci, vol. 91, USA (1994) pp. 10747-10751.
Bowie et al. Science, 247:1306-1310, 1990, p. 1306, col. 2.
Burgess et al., J of Cell Bio. 111:2129-2138, 1990.
Campana et al., "Secretion of prosaposin, a multifunctional protein, by breast cancer cells," Biochimica et Biophysica Acta, 1999: 1427: 392-400.
Egas et al. (J. Biol. Chem. 2000, 275(49): 38190-38196).
Lazar et al. Molecular and Cellular Biology 8:1247-1252, 1988.
Moore et al. (1997) J. Mol. Biol. 272:336-347.
Morimoto et al. (J. Bio. Chem., 1990, 265(4): 1933-1937).
Morimoto et al. (Proc. Natl. Acad. Sci. U.S.A., 1989: 86: 3389-3393).
Needleman and Wunsch (1970) J. MOl. Biol. 48:443-453, the homology alignment algorithm.
Ngo et al., in The Protein Folding Problem and Tertiary Structure Prediction, 1994, Merz, et al., (ed.), Birkhauser, Boston, MA, pp. 433 and 492-495.
Pearson et al., Meth. Mol. Biol., vol. 24 (1994) pp. 365-389.
Qi et al. (J. Biol. Chem., 1996, 271(12): 6874-6880.
Stemmer, Nature, vol. 370 (1994) pp. 389-391.
Vaccaro et al. (FEBS 1993, 336(1): 159-162).
Vaccaro et al., J. Biol. Chem., vol. 270 (1994) pp. 9953-9960 and 30576-30580.
Walker and Gaastra, eds., Techniques in Molecular Biology, MacMillan Publishing Company, New York (1983).
Woon et al., Cell Calcium, vol. 25(4) (1999) pp. 313-320.
You et al., FEBS Lett., vol. 503 (2001) pp. 97-102.
Zhang et al., Proc. Natl. Acad. Sci., vol. 94, USA (1997) pp. 4504-4509.
Abu-Baker et al: "STructural changes in a binary mixed phospholipid bilayer of DOPG and DOPS upon saposin C Interaction at acidic pH utilizing 31P and 2H solid-state NMR spectroscopy", Biochimca Et Biophysica Acta. Biomembranes, Amsterdam, NL, vol. 1717, No. 1, Nov. 10, 2005 (Nov. 10, 2005), pp. 58-66, XP005171447, ISSN: 0005-2736, DOI: DOI:10.1016/J.BBAMEM.2004.09.014.
Qi Xiaoyang et al: "Cancer-Selective Targeting and Cytotoxicity by Liposomal-Coupled Lysosomal Saposin C Protein", Clinical Cancer Research, vo. 15, No. 18, Sep. 2009 (Sep. 2009), pp. 5840-5851, XP002624168, ISSN: 1078-0432.
Wojton J et al: "Systemic delivery of SapC-DOPS has antiangiogenic and antitumor effects against glioblastoma", Molecular Therapy 2013 Nature Publishing Group GBR, vol. 21, No. 8, Aug. 2013 (Aug. 2013), pp. 1517-1525, ISSN: 1525-0016.
Blanco Victor M et al: "Phosphatidylserine-selective targeting and anticancer effects of SapC-DOPS nanovesicles on brain tumors.", Oncotarget Aug. 30, 2014, vol. 5, No. 16, Aug. 30, 2014 (Aug. 30, 2014), pp. 71-5-7118, ISSN: 1949-2553.
Chu Zhengtao et al: "Saposin C: Neuronal effect and CNS delivery by liposomes", Annals of the New York Academy of Sciences, New York Academy of Sciences, New York, NY, US, Jan. 1, 2005 (Jan. 1, 2004), pp. 237-246, XP009107488, ISSN: 0077-8923, DOI: DOI:10.1196/ANNALS.1344.021.
European Patent Office Action dated Nov. 17, 2015.
Australian Patent Office Action dated Nov. 30, 2012.

* cited by examiner

Normal Immortalized Keratinocytes (NIK)

(A) No saposin C and DOPS (B) Saposin C (8μM) + DOPS (26μM)

Squamous Cell Carcinomas (SCC)

(C) No saposin C and DOPS (D) Saposin C (8μM) + DOPS (26μM)

(A)

(B)

(A)

(B)

(C)

(D)

```
SEQUENCE LISTING

<160> NUMBER OF SEQ ID NOS: 2

<210> SEQ ID NO 1
<211> LENGTH: 523
<212> TYPE: PRT
<213> ORGANISM: Homo sapiens

<400> SEQUENCE: 1

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
                20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
    115                 120                 125

Gly Glu Val Cys Ser Ala Leu Asn Leu Cys Glu Ser Leu Gln Lys His
130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190
```

```
Asp Gly Asp Val Cys Gln Asp Cys Ile Gln Met Val Thr Asp Ile Gln
            195                 200                 205

Thr Ala Val Arg Thr Asn Ser Thr Phe Val Gln Ala Leu Val Glu His
    210                 215                 220

Val Lys Glu Glu Cys Asp Arg Leu Gly Pro Gly Met Ala Asp Ile Cys
225                 230                 235                 240

Lys Asn Tyr Ile Ser Gln Tyr Ser Glu Ile Ala Ile Gln Met Met Met
                245                 250                 255

His Met Gln Pro Lys Glu Ile Cys Ala Leu Val Gly Phe Cys Asp Glu
            260                 265                 270

Val Lys Glu Met Pro Met Gln Thr Leu Val Pro Ala Lys Val Ala Ser
    275                 280                 285

Lys Asn Val Ile Pro Ala Leu Asp Leu Val Asp Pro Ile Lys Lys His
290                 295                 300

Glu Val Pro Ala Lys Ser Asp Val Tyr Cys Glu Val Cys Glu Phe Leu
305                 310                 315                 320

Val Lys Glu Val Thr Lys Leu Ile Asp Asn Asn Lys Thr Glu Lys Glu
                325                 330                 335

Ile Leu Asp Ala Phe Asp Lys Met Cys Ser Lys Leu Pro Lys Ser Leu
            340                 345                 350

Ser Glu Glu Cys Gln Glu Val Val Asp Thr Tyr Gly Ser Ser Ile Leu
    355                 360                 365

Ser Ile Leu Leu Glu Glu Val Ser Pro Glu Leu Val Cys Ser Met Leu
370                 375                 380

His Leu Cys Ser Gly Thr Arg Leu Pro Ala Leu Thr Val His Val Thr
385                 390                 395                 400

Gln Pro Lys Asp Gly Gly Phe Cys Glu Val Cys Lys Lys Leu Val Gly
                405                 410                 415

Thr Leu Asp Arg Asn Leu Glu Lys Asn Ser Thr Lys Gln Glu Ile Leu
            420                 425                 430

Ala Ala Leu Glu Lys Gly Cys Ser Phe Leu Pro Asp Pro Tyr Gln Lys
    435                 440                 445

Gln Cys Asp Gln Phe Val Ala Glu Tyr Glu Pro Val Leu Ile Glu Ile
450                 455                 460

Leu Val Glu Val Met Asp Pro Ser Phe Val Cys Leu Lys Ile Gly Ala
465                 470                 475                 480

Cys Pro Ser Ala His Lys Pro Leu Leu Gly Thr Glu Lys Cys Ile Trp
                485                 490                 495

Gly Pro Ser Tyr Trp Cys Gln Asn Thr Glu Thr Ala Ala Gln Cys Asn
            500                 505                 510

Ala Val Glu His Cys Lys Arg His Val Trp Asn
    515                 520

<210> SEQ ID NO 2
<211> LENGTH: 80
<212> TYPE: PRT
<213> ORGANISM: Homo sapiens

<400> SEQUENCE: 2

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45
```

```
Glu Val Val Asp Thr Tyr Gly Ser Ser Ile Leu Ser Ile Leu Leu Glu
50                  55                  60

Glu Val Ser Pro Glu Leu Val Cys Ser Met Leu His Leu Cys Ser Gly
65              70                  75                  80
```

SAPOSIN C-DOPS: A NOVEL ANTI-TUMOR AGENT

CROSS-REFERENCE TO RELATED APPLICATIONS

This application claims priority as a divisional application to U.S. patent application Ser. No. 12/332,809, filed on Dec. 11, 2008 (now U.S. Pat. No. 8,937,156), which is a continuation of U.S. patent application Ser. No. 10/801,517, filed on Mar. 16, 2004 know U.S. Pat. No. 7,834,147), which claims priority to and benefit of U.S. Provisional Application No. 60/466,166, filed on Apr. 28, 2003, which applications are hereby incorporated by reference in their entirety for all purposes.

GOVERNMENT GRANT INFORMATION

This invention was made with government support under DK057690 awarded by the National Institutes of Health. The government has certain rights in the invention.

FIELD OF THE INVENTION

The present invention is directed to compositions for and methods of modulating proliferating cell volume, more particularly to modulating tumor and cancer volume. Additionally the invention is directed to compositions for and methods of treating cancer.

BACKGROUND OF THE INVENTION

Saposins, a family of small (~80 amino acids), heat stable glycoproteins, are essential for the in vivo hydrolytic activity of several lysosomal enzymes in the catabolic pathway of glycosphingolipids (see Grabowski et al. (1990) *Crit. Rev. Biochem. Mol. Biol.* 25:385-414; Furst et al. (1992) *Biochim. Biophys. Acta.* 1126:1-16; Kishimoto et al. (1992) *J Lipid Res.* 33:1255-1267). Four members of the saposin family (A, B, C, and D) are proteolytically hydrolyzed from a single precursor protein, prosaposin (see Fujibayashi et al. (1985) *Am. J Hum. Genet.* 37:741-748; O'Brien et al. (1988) *Science* 241:1098-1101; Rorman et al. (1989) *Genomics* 5:486-492; Nakano et al. (1989). *J Biochem. (Tokyo)* 105: 152-154; Reiner et al. (1989) *J Mol. Neurosci.* 1:225-233; herein incorporated by reference. The complete amino acid sequences for saposins A, B, C, and D have been reported as well as the genomic organization and cDNA sequence of prosaposin (see Fujibayashi et ai. (1985) *Am. J Hum. Genet.* 37:741-748; O'Brien et ai. (1988) *Science* 241:1098-1101; Rorman et al. (1989) *Genomics* 5:486-492).

Saposins are defined as sphingolipid activator proteins or coenzymes. Structurally, saposins A, B, C, and D have approximately 50-60% similarity including six strictly conserved cysteine residues (see Furst et al. (1992) *Biochim. Biophys. Acta* 1126:1-16) that form three intradomain disulfide bridges whose placements are identical (see Vaccaro et al. (1995) *J. Biol. Chem.* 270:9953-9960). All saposins contain one glycosylation site with conserved placement in the N-terminal sequence half, but glycosylation is not essential to their activities (see Qi et al. (1998) *Biochemistry* 37:11544-11554 and Vaccaro et al. (1995) *J. Biol. Chem.* 270:30576-30580, herein incorporated by reference in their entirety).

All saposins and saposin-like proteins and domains contain a "saposin fold" when in solution. This fold is a multiple a-helical bundle motif, characterized by three conserved disulfide structures and several amphipathic polypeptides. Despite this shared saposin-fold in solution, saposins and saposin-like proteins have diverse in vivo biological functions in the enhancement of lysosomal sphingolipid (SL) and glycosphingolipid (GSL) degradation by specific hydrolases. Because of these roles, the saposins occupy a central position in the control of lysosomal sphingolipid and glycosphingolipid metabolisms (see Kishimoto et al. (1992) *J. Lipid Res.* 33:1255-1267; Fujibayashi et al. (1985) *Am. J. Hum. Genet.* 37:741-748; O'Brien et al. (1988) *Science* 241:1098-1101, herein incorporated by reference). In addition, saposins participate in the fusion and destabilization of acidic phospholipid vesicles (see Vaccaro et al. (1994) *FEBS Letters* 349:181-186, herein incorporated by reference).

Saposin C is required for optimal hydrolysis of glucosylceramide by acid β-glucosidase (Gcase, EC 3.1.2.45) in vivo and in vitro. Also, saposin C induced fusion toward phosphatidylserine containing vesicles has been observed by electron microscopy (see Vaccaro et al. (1994) *FEBS Letters* 349:181-186, herein incorporated by reference). Further, saposin C has the general property of lipid membrane binding activity or plasma membrane affinity. Saposins associate with lipid membranes by embedding into the outer leaflets. The H-1 and H-5 helices are integral to this process, suggesting that proper membrane interaction of saposin C affects its specificity and activity. In addition, saposin C induces structural changes of the membrane. The dynamic processes of saposin interactions with planar phospholipid bilayers have been visualized in real time using atomic force microscopy (see Qi et al. (2001) *J. Biol. Chem.* 276:27010-27017 and You et al. (2001) *FEBS Lett.* 503:97-102, herein incorporated by reference).

Phospholipid asymmetry is a well-known characteristic of mammalian plasma membranes. The outer leaflet of the lipid bilayer is rich in choline-phospholipids, whereas aminophospholipids are preferentially in the inner leaflet (Bevers et al. (1998) *Lupus Suppl.* 2:S126-S131). Phosphatidylserine (PS) and phosphatidylethanolamine (PE) reside almost exclusively in the inner leaflet, and phosphatidylcholine (PC) and sphingomyelin are enriched in the outer leaflet. Phospholipid asymmetry might be a general property of all cells (Woon et al. (1999) *Cell Calcium* 25(4):313-320). The plasma membrane phospholipid asymmetry is maintained through a variety of mechanisms, including aminophospholipid translocases and phospholipid scramblases (U.S. Patent Application No: 20020081698).

In general, tumor or cancer cells grow rapidly in comparison to normal cells. These abnormal cells produce a significant amount of protons primarily by generating lactic acid during glycolysis or by generating carbon dioxide during respiration due to a fast metabolic rate. Therefore, the surrounding sites of these cells and tissues are usually found to be more acidic than those of cells with a normal growth rate.

Squamous cell carcinomas (SCCs) of the skin are one of the most common skin cancers associated with a substantial risk of metastasis (Alam et al. (2001) *N. Engl. J. Med.* 344:975-983, herein incorporated by reference). Cancers of the skin are classified into two categories, melanoma and non-melanoma skin cancers (NMSC). According to the estimation by the American Cancer Society, more than one million cases of NMSC are found in the United States each year. SCC accounts for approximately 20% of all cutaneous tumors and there are about 200,000 new SCC cases in the United States each year. SCC is the most frequent form of malignant tumor in the transition from the skin to the mucosa and in the mucosa itself (Boni et al. (2002) *Neu-* roendocrinology Letters 23S2:48-51). The current treatments of SCC patients include electrodessication and curettage, excision, cryotherapy, surgical excision, or Mohs' surgery. Appropriate use of electrodessication and curettage, excision, or cryotherapy can eliminate small (<1 cm in diameter), well-defined tumors with a low risk of metastasis. Surgical excision and Mohs' surgery offer the highest rates of cure for patients with high-risk primary or recurrent SCCs. However, these treatments are more costly with the risk of hematoma, seroma, infection, and wound dehiscence.

Thus, development of an effective, low-cost SCC treatment with improved cosmetic outcomes is desirable. It is also of importance to develop an effective, low-cost treatment for other cancer types such as breast and prostate cancers and lymphomas.

SUMMARY OF THE INVENTION

Compositions and methods for modulating distribution of components of the inner and outer leaflets of plasma membranes are provided. Agents of the invention comprise an inner leaflet component and a prosaposin related polypeptide. By "inner leaflet component" is intended any molecule or structural analog thereof naturally occurring in the inner leaflet of a plasma membrane of a cell, particularly an animal cell, more particularly a mammalian cell. In an embodiment the inner leaflet component is phosphatidylserine or a structural analog thereof, such as dioleoylphosphatidylserine (DOPS). The amino acid sequence of prosaposin is set forth in SEQ ID NO:1 in the sequence listing. Prosaposin related polypeptides share at least 80% identity to the amino acid sequence set forth in SEQ ID NO:1 or a fragment thereof and retain plasma-membrane affinity. In an embodiment, the prosaposin related polypeptide is saposin C (SEQ ID NO:2 of the sequence listing) or a saposin C-related polypeptide. Saposin C-related polypeptides share at least 80% identity to the amino acid sequence set forth in SEQ ID NO:2 and retain plasma-membrane affinity. The molar ratio of the polypeptide to the inner leaflet component in an agent of the invention is in the range from about 1:1 to about 1:50, preferably about 1:1 to about 1:25, more preferably about 1:1 to about 1:10, yet more preferably about 1:7 or about 1:3. In an embodiment, agents of the invention further comprise a pharmaceutically acceptable carrier. An agent of the invention promotes cell death, such as cell death through apoptosis. In an embodiment, the agent preferentially induces in apoptosis in hyper-proliferating cells such as, but not limited to, tumor and cancer cells. Thus, in an embodiment of the invention, the agent is an anti-tumor agent. In an aspect of the invention, the agent preferentially induces apoptosis in cancer cells such as, but not limited to, sarcoma cells, neuroblastoma cells, and squamous cell carcinoma cells.

Methods for modulating the distribution of an inner leaflet component in the plasma membrane of a cell of a subject are provided. Such methods involve administering an agent comprising an inner leaflet component and a prosaposin related polypeptide to a subject. The methods alter the distribution of the inner leaflet component in the outer leaflet of a plasma membrane of a cell of the subject. In an embodiment, the concentration of the inner leaflet component in the outer leaflet is increased. In an embodiment of the invention, modulating the distribution of an inner leaflet component preferentially occurs in hyper-proliferating cells of the subject. Preferably such hyper-proliferating cells are tumor cells or cancer cells. In an aspect of the invention, modulating the concentration of an inner leaflet component in the outer leaflet of the plasma membrane induces apoptosis.

Methods for modulating tumor volume in a subject are provided. Such methods involve administering an agent comprising an inner leaflet component and a prosaposin related polypeptide to a subject. The agent may further comprise a pharmaceutically acceptable carrier. Suitable subjects include mammals, particularly humans, with tumors. In an embodiment, the agent promotes cell death in hyper-proliferating cells. Cell death may occur through apoptosis. Any tumor is a potential target of the invention. The target tumors contain hyper-proliferating cells such as tumor cells and cancer cells. Such target tumors include, but are not limited to, sarcomas, neuroblastomas, and squamous cell carcinomas. In an embodiment, modulating the tumor volume results in a decrease in tumor volume. It is envisioned that the death of hyper-proliferating cells within the tumor results in a decrease in tumor volume.

Methods for treating a cancer in a subject are provided. Such methods involve administering an agent comprising an inner leaflet component and a prosaposin related polypeptide to a subject. The agent may further comprise a pharmaceutically acceptable carrier. Suitable subjects include mammals, particularly humans, with cancers. In an embodiment, the agent promotes cell death in hyper-proliferating cells. Cell death occurs through a process such as, but not limited to, apoptosis. Any cancer is a potential target of the invention. Target cancers contain hyper-proliferating cells such as tumor and cancer cells. Target cancer cells include, but are not limited to, cells derived from sarcomas, neuroblastomas, breast carcinomas, and squamous cell carcinomas. In an aspect of the invention, the agent is administered enterally, parenterally, subcutaneously, intravenously, intraperitoneally, or topically. Either a single or multiple doses of the agent may be administered to a subject to treat a cancer.

DETAILED DESCRIPTION OF THE INVENTION

Figure 1:
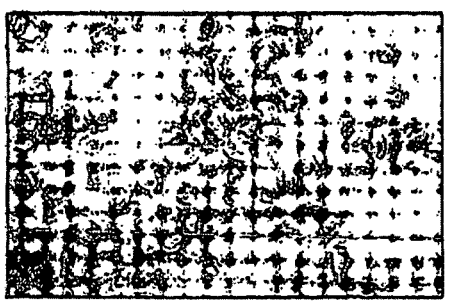
FIG. 1 presents normal immortalized keratinocytes (NIK) (Panels A and B) and squamous cell carcinoma cells (SCC) (Panels C and D). The cells in Panels A and C received placebo treatments. The cells in Panels B and D were treated with an agent of the invention comprising 8 μM saposin C and 26 μM DOPS. Details of the experiment are described elsewhere herein.
Figure 1:
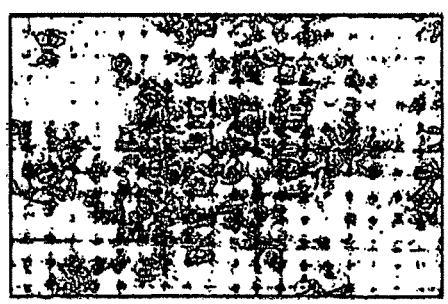
Figure 1:
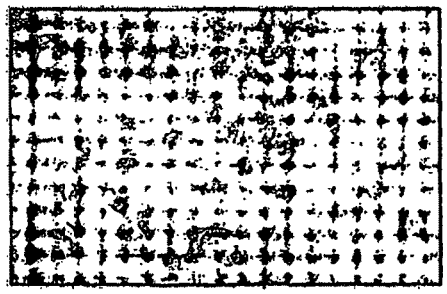
Figure 1:

The present invention relates to compositions and methods for modulating the distribution of inner leaflet components in a plasma membrane. Further, the present invention relates to compositions and methods for modulating hyperproliferating cells, particularly disorders involving hyperproliferating cells, more particularly tumors and cancers such as squamous cell carcinomas and lymphomas. The compositions comprise an agent with a prosaposin-related polypeptide, particularly saposin C, and an inner leaflet component, particularly a phosphatidylserine or structural analog thereof, more particularly dioleoylphosphatidylserine (DOPS). Combinations of these two compounds exhibit anti-tumor activity and hence are referred to as anti-tumor agents. By "anti-tumor activity" is intended a reduction in the rate of cell proliferation, and hence a decline in the growth rate of an existing tumor or in a tumor that arises during therapy, and/or destruction of existing neoplastic (tumor) cells or newly formed neoplastic cells, and hence a decrease in the overall size of a tumor during therapy. Treatment with a combination of saposin C (or a prosaposin-related polypeptide) and DOPS (or an inner leaflet component) causes a physiological response that modulates the distribution of an inner leaflet component in the plasma membrane.

The anti-tumor activity of an agent of the invention is not limited to a particular mode of action, but may function through a variety of modes of action including but not limited to, apoptosis. Environmental factors contribute to the agent's preferential effect on tumor cells. These environmental factors include, but are not limited to, lower pH levels near tumor cells, increasing hypoxic conditions, and altered lipid presentation on the outer membrane of tumor cells. Hypoxia is an epigenetic factor that stimulates expression and release of vascular endothelial growth factor (VEGF) from tumor cells. VEGF is known in the art as a vascular permeability factor and may play a role in the disorganized and leaky vasculatures of tumor tissues as compared to normal vasculature. In an embodiment, a saposin C-DOPS agent of the invention preferentially penetrates tumor tissue rather than healthy tissue after intravenous administration.

The invention encompasses isolated or substantially purified protein or polypeptide compositions. An "isolated" or "purified" polypeptide or biologically active portion thereof, is substantially or essentially free from components that normally accompany or interact with the protein as found in its naturally occurring environment. Thus, an isolated or purified protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

As used herein, a "prosaposin-related polypeptide" is any polypeptide having the prosaposin amino acid sequence set forth in SEQ ID NO:1, an amino acid sequence at least 80% identical to the amino acid sequence set forth in SEQ ID NO:1, or a proteolytically processed fragment thereof, wherein said polypeptide retains plasma membrane affinity. Fragments and variants of the prosaposin polypeptide (SEQ ID NO: 1) are also encompassed by the present invention. Prosaposin is proteolytically processed into four saposins, saposins A, B, C, and D. As used herein, a "saposin C-related polypeptide" is any polypeptide having the saposin C amino acid sequence set forth in SEQ ID NO:2 or an amino acid sequence at least 80% identical to the amino acid sequence set forth in SEQ ID NO:2, wherein said polypeptide retains plasma membrane affinity. Fragments and variants of the saposin C-related polypeptide (SEQ ID NO:2) are also encompassed by the present invention. By "fragment" is intended a portion of the amino acid sequence and hence protein. Prosaposin protein fragments retain the biological activity of prosaposin and hence possess plasma membrane affinity. Saposin C protein fragments retain the biological activity of saposin C and hence possess plasma membrane affinity. As used herein "plasma membrane affinity" refers to an ability to interact with phospholipid surfaces through electrostatic or hydrophobic interactions.

A fragment of a biologically active portion of prosaposin polypeptide of the invention will encode at least 15, 25, 30, 35, 40, 45, 50, 55, 60, 65, 70, 75, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520 continuous amino acids, or up to 524 amino acids present in a prosaposin polypeptide of the invention. A fragment of a biologically active portion of saposin C polypeptide of the invention will encode at least 15, 25, 30, 35, 40, 45, 50, 55, 60, 65, 70, 75, or 80 contiguous amino acids present in a saposin C polypeptide of the invention.

By "variants" is intended substantially similar sequences. For nucleotide sequences, conservative variants include those sequences that, because of the degeneracy of the genetic code, encode the amino acid sequence of a prosaposin polypeptide of the invention. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis but which still encode a prosaposin.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; substitution of one or more amino acids at one or more sites in the native protein, or synthetically produced polypeptides having such an amino acid sequence. Variant proteins encompassed by the present invention are biologically active, that is they continue to possess the desired biological activity of the native protein, that is, plasma membrane affinity as described herein. Such variants may result from, for example, genetic polymorphism or from human manipulation. Biologically active variants of a native prosaposin protein of the invention will have at least about 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the prosaposin protein can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.) and Qi et al. (2001) *J. Biol. Chem.* 276:27010-27017, herein incorporated by reference. Conservative substitutions, such as exchanging one amino acid with another having similar properties, may be preferable.

Thus, the polypeptide and amino acid sequences of the invention include both the naturally occurring sequences as well as mutant forms, variants, and modified forms thereof Such variants will continue to possess the desired plasma membrane affinity activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the plasma membrane affinity can be evaluated by methods known in the art including, but not limited to, fluorescence spectrophotometry, fluorescence resonance energy transfer, or circular dichroism measurements. See, for example, Qi et al. (2001) *J. Biol. Chem.* 276:27010-27017, herein incorporated by reference.

Variant proteins also encompass proteins derived from a mutagenic and recombinogenic procedure such as DNA shuffling. With such a procedure, one or more different saposin C sequences can be manipulated to create a new saposin C possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the prosaposin gene of the invention and other known prosaposin genes to obtain a new gene coding for a protein with an improved property of interest, such as an altered plasma membrane affinity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more amino acid sequences or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length polypeptide or amino acid sequence or the complete polypeptide sequence.

(b) As used herein "comparison window" makes reference to a contiguous and specified segment of an amino acid sequence, wherein the amino acid sequence in the comparison window may comprise additions or deletions (i.e. gaps) compared to the reference sequence (which does not comprise additions or deletions) for optimal alignment of the two sequences. Generally the comparison window is at least 20 contiguous amino acids in length, and optionally can be 30, 40, 50, 100, or longer. Those of skill in the art understand that to avoid a high similarity to a reference sequence due to inclusion of gaps in the amino acid sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. For purposes of the present invention, comparison of nucleotide or protein sequences for determination of percent sequence identity to the sequences disclosed herein is preferably made using the GCG program GAP (Version 10.00 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Sequence comparison programs include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. National Center for Biotechnology Information (NCBI). Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) J. Mol. Biol. 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Agents of the invention comprise a prosaposin-like polypeptide and an inner leaflet component. By "inner leaflet component" is intended any molecule or structural analog thereof naturally occurring in the inner leaflet of a plasma membrane of a cell, particularly an animal cell, more particularly a mammalian cell. In general the concentration of an inner leaflet component in the inner leaflet will be greater than the concentration of that inner leaflet component in the outer leaflet. It is recognized that during certain cellular perturbations such as apoptosis, necrosis, and hyper-proliferative growth the normal composition of the inner and outer leaflets are altered. Exemplary inner leaflet components include, but are not limited to, phosphatidylserine, phosphatidylethanolamine, and structural analogs thereof. By "structural analog" of phosphatidylserine is intended any anionic phospholipid or acid lipid with a negatively charged head group including, but not limited to, phosphatidic acid, phosphatidylglycerol, phosphatidylinositol, palmitoyloleoylphosphatidylserine, palmitelaidoyloleoylphosphatidylserine, myristoleoyloleoylphosphatidylserine, dilinoleoylphosphatidylserine, palmiticlinoleoylphosphatidylserine, lysophosphatidylserine, and dioleoylphosphatidylserine.

In an embodiment the compositions and methods of the invention are directed toward modulating inner leaflet component distribution in a plasma membrane. In another embodiment, the compositions and methods of the invention are directed to the modulation and treatment of disorders involving hyper-proliferating cells such as tumors and cancers. By "modulate" is intended alter, change, vary, modify, or permute by at least 0.01%, 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. Modulating the distribution of an inner leaflet component in a plasma membrane alters the amount of the component in the plasma membrane, alters the relative location of the component in the inner leaflet, or alters the percentages of the component found in the inner leaflet and outer leaflet of the plasma membrane. Such a modulation may result in an increase of the inner leaflet component concentration in the outer leaflet of the plasma membrane. Modulating tumor volume alters the tumor volume, the volume of at least one tumor cell, or the number of tumor cells.

Methods of assaying component distribution in a plasma membrane are known in the art and include, but are not limited to, confocal microscopy, atomic force microscopy, FRET, fluorescence dequenching, electron microscopy, circular dichroism, NMR, MALDI-TOF, emission spectra analysis, light-scattering, electrospray-mass spectrometry. See Chang et al. (1978) *Anal. Biochem.* 91:13-31; Kishimoto et al. (1992) *J. Lipid Research* 33:1255-1267; Vaccaro et al. (1995) *J. Biol. Chem.* 270:9953-9960; and Fu et al. (1994) *J. Mol. Neurosci.* 5:59-67, herein incorporated by reference in their entirety.

Methods of assaying tumor volume are known in the art and include, but are not limited to, caliper measurements, volumetry, ultrasounds, magnetic resonance imagery, ELISAs, physical examination, X-rays, positron emission tomography, bone scans, resonance Raman spectroscopy, tactile imagery, computerized tomography, and CAT scans.

As used herein, the terms "cancer", "hyper-proliferative," "tumor," and "neoplastic" refer to cells having the capacity for autonomous growth, i.e., an abnormal state or condition characterized by rapidly proliferating cell growth. Hyper-proliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The term hyper-proliferative further includes smooth muscle cells undergoing rapid proliferating cell growth such as occurs in certain cardiomyopathies. "Pathologic hyper-proliferative" cells occur in disease states characterized by malignant tumor growth. Examples of non-pathologic hyper-proliferative cells include proliferation of cells associated with wound repair.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

The terms "cancer" or "neoplasms" include malignancies of the various organ systems, such as those affecting the lung, breast, thyroid, lymphoid, gastrointestinal, or genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Tumors and cancers of the skin include, but are not limited to, malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis.

Tumors and cancers of cells found in the bone marrow include, but are not limited to, disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including Kaposi's sarcoma; fibroadenoma and phyllodes tumors, including mammary fibroadenoma; stromal tumors; phyllodes tumors, including histiocytoma; T-cell lymphomas; and B-cell lymphomas.

Tumors and cancers of the heart include, but are not limited to, primary cardiac tumors, such as myxoma, lipoma, papillary fibroelastoma, rhabdomyoma, and sarcoma, and cardiac effects of noncardiac neoplasms.

Tumors and cancers of the blood vessels include, but are not limited to hemangioma, lymphangioma, glomus tumor (glomangioma), vascular ectasias, and bacillary angiomatosis, and intermediate-grade (borderline low-grade malignant) tumors, such as Kaposi sarcoma and hemangioendothelioma, and malignant tumors, such as angiosarcoma and hemangiopericytoma.

Tumors and cancers of the B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Tumors and cancers of the liver include, but are not limited to nodular hyperplasias, adenomas, and malignant tumors, including primary carcinoma of the liver and metastatic tumors.

Tumors and cancers of the brain include, but are not limited to gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromatosis, including Type 1 neurofibromatosis (NF1) and TYPE 2 neurofibromatosis (NF2), tuberous sclerosis, and Von Hippel-Lindau disease.

Tumors and cancers of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Tumors and cancers of the kidney include, but are not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Tumors and cancers of the skeletal muscle include, but are not limited to, rhabdomyosarcoma.

Tumors and cancers of the bone-forming cells include, but are not limited to, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Tumors and cancers of the pancreas include, but are not limited to, cystic tumors and carcinoma of the pancreas; islet cell tumors, including but not limited to, insulinomas, gastrinomas, and other rare islet cell tumors.

Tumors and cancers of the breast include, but are not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Tumors and cancers of the male breast include, but are not limited to, carcinoma.

Tumors and cancers of the prostate include, but are not limited to, carcinoma.

Tumors and cancers of the colon include, but are not limited to, non-neoplastic polyps, adenomas, familial syndromes, colorectal carcinogenesis, colorectal carcinoma, and carcinoid tumors.

Tumors and cancers of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pleural tumors, including solitary fibrous tumors (pleural fibroma) and malignant mesothelioma.

Tumors and cancers of the thymus include, but are not limited to, thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Tumors and cancers of the tonsils include, but are not limited to, non-Hodgkin's lymphoma and B-cell lymphoma.

An agent of the invention comprising a prosaposin related polypeptide and an inner leaflet component (also referred to herein as "active compounds") can be incorporated into pharmaceutical compositions suitable for administration to a subject. Such compositions typically comprise a prosaposin related polypeptide, an inner leaflet component, and a pharmaceutically acceptable carrier. In an embodiment the prosaposin related polypeptide and the inner leaflet component form a nanovesicle. The nanovesicle diameter is in the range 0.01 to 10 µm, preferably 0.1 to 1 µm, more preferably 0.1 to 0.5 µm, yet more preferably 0.2 to 0.4 µm, yet still more preferably 0.2 to 0.3 μm. Typical nanovesicle diameters include, but are not limited to, 10 nm, 100 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 350 nm, 400 nm, 450 nm, 500 nm, 550 nm, 600 nm, 650 nm, 700 nm, 750 nm, 800 nm, 850 nm, 900 nm, 950 nm, and 1000 nm.

The term "administer" is used in its broadest sense and includes any method of introducing the compositions of the present invention into a subject. By "subject" is intended a mammal, e.g., a human, or an experimental or animal or disease model. The subject can also be a non-human animal such as, but not limited to, a non-human primate, horse, cow, goat, pig, rabbit, mouse, guinea pig, dog, or other domestic animal. Additionally the compositions of the invention find use in the treatment of disorders described herein. Thus, therapies for disorders associated with hyper-proliferating cells such as tumors or cancers are encompassed herein. "Treatment" is herein defined as the application or administration of an agent of the invention to a patient, or application or administration of an agent of the invention to an isolated tissue or cell line from a patient, who has a disease or symptom of a disease, with the purpose to cure, heal, alleviate, relieve, alter, remedy, ameliorate, improve, or affect the disease or symptoms of the disease.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

An anti-tumor agent or pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compounds (e.g., a prosaposin-related polypeptide and an inner leaflet component) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of an agent of the invention is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

The anti-tumor or anti-cancer agents described herein can be administered transdermally. Transdermal administration typically involves the delivery of a pharmaceutical agent for percutaneous passage of the drug into the systemic circulation of the subject or patient. The skin sites include anatomic regions for transdermally administering the drug and include the forearm, abdomen, chest, back, buttock, mastoidal area, and the like.

Transdermal delivery is accomplished by exposing a source of the agent or complex to a patient's skin for an extended period of time. Transdermal patches have the added advantage of providing controlled delivery of a pharmaceutical agent to the body (see Hadgraft and Guy (eds) (1989) *Transdermal Drug Delivery: Developmental Issues and Research Initiatives*, Marcel Dekker, Inc.; Robinson & Lee (eds) (1987) *Controlled Drug Delivery: Fundamentals and Applications*, Marcel Dekker, Inc; and Kydonieus & Berner (eds) (1987) *Transdermal Delivery of Drugs* vols 1-3, CRC Press, herein incorporated by reference). Such dosage forms can be made by dissolving, dispersing, or otherwise incorporating the combination of saposin C related polypeptide and dioleoylphosphatidylserine (DOPS) in a proper medium, such as an elastomeric matrix material. Absorption enhancers can also be used to increase the flux of the compound across the skin. The rate of such flux can be controlled by providing a rate-controlling membrane or dispersing the agent in a polymer matrix or gel.

A variety of types of transdermal patches will find use in the methods described herein. For example, a simple adhesive patch can be prepared from a backing material and an acrylate adhesive. The pharmaceutical agent and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively a polyurethane matrix patch can be employed to deliver the agent. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast on the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

For passive delivery systems, the rate of release is typically controlled by a membrane placed between the reservoir and the skin, by diffusion from a monolithic device, or by the skin itself serving as a rate-controlling barrier in the delivery system (see U.S. Pat. Nos. 4,816,258; 4,927,408; 4,904,475; 4,588,580; 4,788,062, herein incorporated by reference). The rate of drug delivery will be dependent in part upon the nature of the membrane. For example, the rate of drug delivery across membranes within the body is generally higher than across dermal barriers. The rate at which the agent is delivered from the device to the membrane is most advantageously controlled by the use of rate-limiting membranes placed between the reservoir and the skin. When the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the agent, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other pharmaceutically acceptable carriers, depending on the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, and antipruritic agents.

Another aspect of this invention provides for the topical delivery of an agent of the invention. This treatment regimen is suitable either for the systemic administration of the anti-tumor agent or for localized therapy, i.e., directly to pathological or diseased tissue.

Typically, the topical formulations will comprise a preparation for delivering the agent directly to the affected area comprising the complex, typically in concentrations in the range of from about 0.001% to 10%; preferably, from about 0.01 to about 10%; more preferably from about 0.1 to about 5%; and most preferably from about 1 to about 5%, together with a non-toxic, pharmaceutically acceptable topical carrier (Barry (eds). *Dermatological Formulations: Percutaneous Absorption* (1983) Marcel Dekker, Inc; for standard dosages of conventional pharmaceutical agents see, e.g., Physicians Desk Reference (1992 Edition); and American Medical Association (1992) Drug Evaluations Subscriptions).

Topical preparations can be prepared by combining the agent with conventional pharmaceutical diluents and carriers commonly used in topical dry, liquid, cream, and aerosol formulations. Ointment and creams may, for example, be formulated with an aqueous or oily base with the addition of suitable thickening and/or gelling substances. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, wool fat, hydrogenated lanolin, beeswax, and the like. Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable base, e.g., talc, lactose, starch, and the like. Drops may be formulated with an aqueous base or non-aqueous base also comprising one or more dispersing agents, suspending agents, solubilizing agents, and the like.

Dosage forms for the topical administration of an agent of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required.

The ointments, pastes, creams, and gels also may contain excipients, such as animal and vegetable fats, oils, waxes, paraffins, starch, tragacanth, cellulose derivatives, polyethylene glycols, silicones, bentonites, talc, and zinc oxide, or mixtures thereof. Powders and sprays also can contain excipients such as lactose, talc, aluminum hydroxide, calcium silicates, and polyamide powder, or mixtures of those substances. Sprays can additionally contain customary propellants, such as chlorofluorohydrocarbons and volatile unsubstituted hydrocarbons such as butane and propane.

The methods of the present invention are also applicable to the delivery of pharmaceutical agents through mucosal membranes such as a gastrointestinal, sublingual, buccal, nasal, pulmonary, vaginal, corneal, and ocular membranes (Mackay et al. (1991) *Adv. Drug Del. Rev.* 7:313-338).

For delivery to the buccal or sublingual membranes, typically an oral formulation such as a lozenge, tablet, or capsule will be used. The method of manufacture of these formulations are known in the art, including, but not limited to, the addition of the agent to a pre-manufactured tablet; cold compression of an inert filler, a binder, and encapsulation.

Another oral formulation is one that can be applied with an adhesive such as the cellulose derivative, hydroxypropyl cellulose, to the oral mucosa, for example as described in U.S. Pat. No. 4,940,587, incorporated by reference. This buccal adhesive formulation, when applied to the buccal mucosa, allows for the controlled release of an agent into the mouth and through the buccal mucosa.

For delivery to the nasal and/or pulmonary membranes, typically an aerosol formulation will be employed. The term "aerosol" includes any gas-borne suspended phase of an agent of the invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the agent suspended in air or other carrier gas, which may be delivered by inhalation from an inhaler device.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide in the agent (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 15 mg/kg. A therapeutically effective amount of an inner leaflet component in the agent (i.e., an effective dosage) ranges from about 0.001 to 30 mg/kg body weight, preferably from about 0.01 to about 30 mg/kg body weight, more preferably about 0.01 to about 20 mg/kg body weight, yet more preferably 0.01 to 10 mg/kg body weight, and even more preferably about 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, or 0.1 to 3 mg/kg body weight.

The molar ratio of the polypeptide to the inner leaflet component in an agent of the invention is in the range from about 1:1 to about 1:50, preferably about 1:1 to about 1:25, more preferably about 1:1 to about 1:10, yet more preferably about 1:7 or about 1:3. Suitable ratios include, but are not limited to, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:30, 1:35, 1:40, 1:45, and 1:50. The mass ratio of the polypeptide to the inner leaflet component in an agent of the invention is in the range from about 15:1 to about 3:10, preferably about 15:1 to about 3:5, more preferably about 15:2 to about 3:0, yet more preferably about 15:7 or about 5:1. It is recognized that the preferred ratio of the polypeptide and inner leaflet component in an agent of the invention may be affected by certain factors such as, but not limited to, the target cell type.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with a therapeutically effective amount of the agent one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Where a subject undergoing therapy exhibits a partial response or a relapse following a prolonged period of remission, subsequent course of treatment with an agent of the invention may be administered. Thus, subsequent to a period of time off from a first treatment period, which may have comprised a single dosing regimen or a multiple dosing regimen, a subject may receive one or more additional treatment periods comprising single or multiple dosing regimens. Such a period of time off between treatment periods is referred to herein as a time period of discontinuance. It recognized that the length of the time period of discontinuance is dependent upon the degree of tumor response achieved with any prior treatment periods with the anti-tumor agents of the invention.

The pharmaceutical compositions can be included in a container, pack, or dispenser together with instructions for administration.

The results of treatment of a cancer may be assayed by any method known to one skilled in the art including, but not limited to, physical examination, laboratory, nuclear, and radiographic studies (i.e. computer tomography and/or magnetic resonance imagery), ultrasound and other procedures.

As used herein "cell death" refers to loss of cell life through any mechanism including apoptosis, necrosis, and lysis. By "apoptosis" or "programmed cell death" is intended a normal physiological process requiring regulated metabolic activity by the dying cell, often characterized by cell shrinkage, chromatin condensation, and/or nuclear fragmentation, loss of membrane integrity, DNA fragmentation, and/or compromised or blebbing of plasma membranes.

The following examples are offered by way of illustration and not limitation.

EXPERIMENTAL

Example 1. Purification of Recombinant Saposin C

Recombinant saposin C was overexpressed in *E. coli* cells by using the isopropyl-1-thio-β-D-galactopyranoside inducing pET system (Qi et al. (1994) *J. Biol. Chem.* 269:16746-16753, herein incorporated by reference in its entirety). Expressed polypeptides with a His-tag were eluted from nickel columns. After dialysis, the polypeptides were further purified by HPLC chromatography as follows. A C4 reverse phase column was equilibrated with 0.1% trifluoroacetic acid (TFA) for 10 minutes. The proteins were eluted in a linear (0-100%) gradient of 0.1% TFA in acetonitrile over 60 minutes. The major protein peak was collected and lyophilized. Protein concentration was determined as previously described (Qi et al. (1994) *J. Biol. Chem.* 269:16746-16753).

Example 2. Bath Sonication of Saposin C and Dioleoylphosphatidylserine

Dioleoylphosphatidylserine (DOPS) was obtained from Avanti Polar Lipids (Alabaster Ala.). Twenty to thirty μmoles of DOPS in chloroform were dried under $N_2$ and vacuum to lipid films. Five to ten μmoles saposin C polypeptide was added to the dried films and suspended in 50 μl McIlvanine buffer (pH 4.7). The suspension was then brought to a 1 ml volume with either cell culture medium or phosphate buffered saline (PBS) (Ausubel et al. (2002) *Current Protocols in Molecular Biology*. John Wiley & Sons, New York, N.Y., herein incorporated by reference). The mixture was sonicated in a bath sonicator for approximately 20 minutes. Ice was added as needed to prevent overheating the samples.

Example 3. Tissue Culture Conditions

Squamous cell carcinoma (SCC) cells and L5178Y cells were cultured in DEME medium (Gibco) supplemented with 10% FBA. Normal Immortalized Keratinocytes (NIK) cells were grown in 50% Cascade medium 154 (Cascade Biologics) and 50% Keratinocyte-SFM medium (Gibco).

Example 4. Ex Vivo Analysis of Effects of Saposin C-DOPS on SCC Cells

Squamous cell carcinoma (SCC) cells and control (NIK cells) were grown in media described elsewhere herein. NIKs were used as a control, since SCC have been suggested to develop through a multistep process in human skin keratinocytes (Kubo et al. (2002) *J. Med. Invest.* 49:111-117). Culture medium was removed from established plates of NIK and SCC cells. Culture medium containing no treatment, saposin C, DOPS, or 8 μM saposin C+26 μM DOPS was added to established plates of NIK and SCC cells. The cells were examined 48-72 hours after treatment. Results from one such experiment are presented in FIG. 1.

Squamous cell carcinoma (SCC) cells were grown in media described elsewhere herein. Culture medium was removed from established plates of SCC cells. Culture medium containing no treatment or an agent comprising 10 μM saposin C+30 μM DOPS was added to established plates of SCC cells. The cells were incubated for 24 hours and analyzed by TUNEL staining, gel electrophoresis of genomic DNA, or hybridization assays with the anti-coagulant protein, annexin V, data not shown.

Example 5. Ex Vivo Analysis of Saposin C-DOPS Effect on Murine Lymphoma Cells

Figure 2:
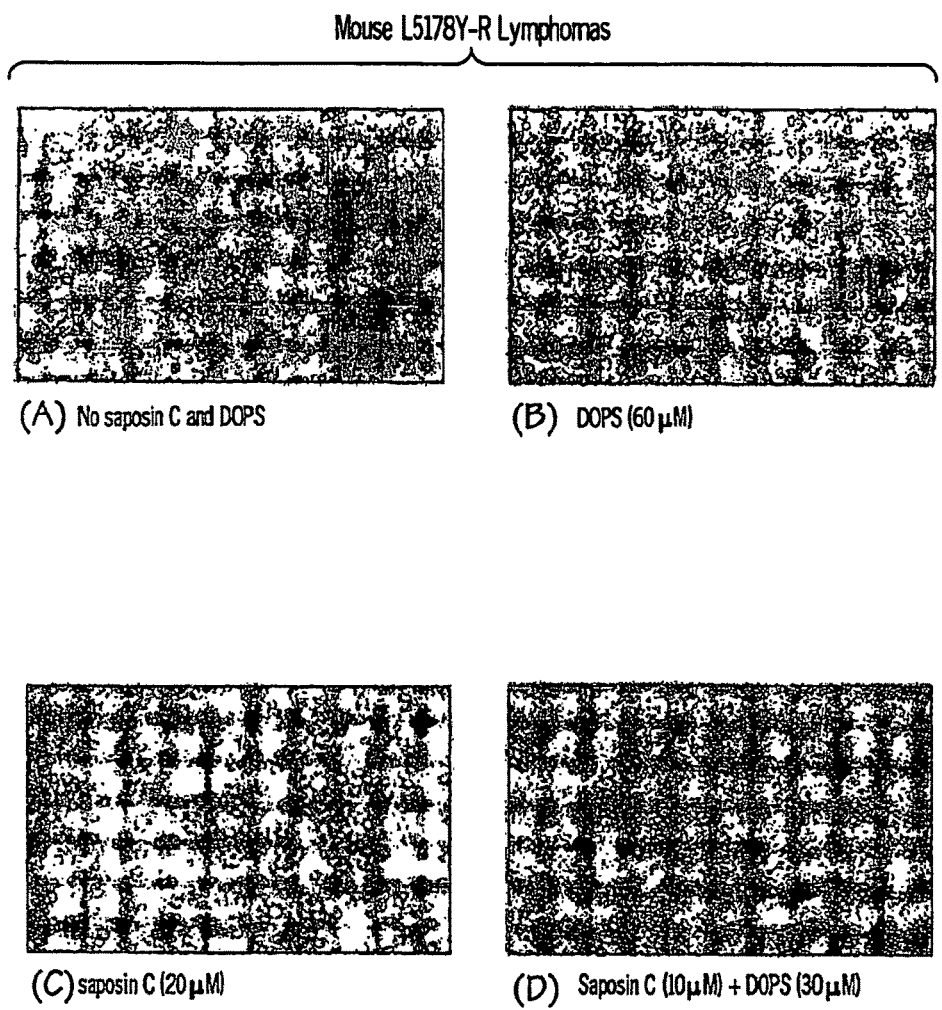
FIG. 2 presents murine lymphoma cells from the L5178Y-R cell line. The cells in Panel A received a placebo treatment. The cells in Panel B were treated with 60 μM DOPS. The cells in Panel C were treated with 20 μM saposin C. The cells in Panel D were treated with an agent of the invention comprising 10 μM saposin C and 30 μM DOPS.

Tissue culture plates were seeded with mouse L5178Y-R lymphoma cells. After establishment of the cultures, the culture media was removed and the cells were washed. The cells were overlaid with DEME+10% FBA supplemented with either no drug, 60 μM DOPS, 20 μM saposin C, or 10 μM saposin C and 30 μM DOPS. The cultures were incubated for 24-48 hours. Cultures were examined after the incubation period. Results from one such experiment are presented in FIG. 2.

Example 6. In Vivo Analysis of Saposin C-DOPS Effect on Tumor Volume

Figure 3:
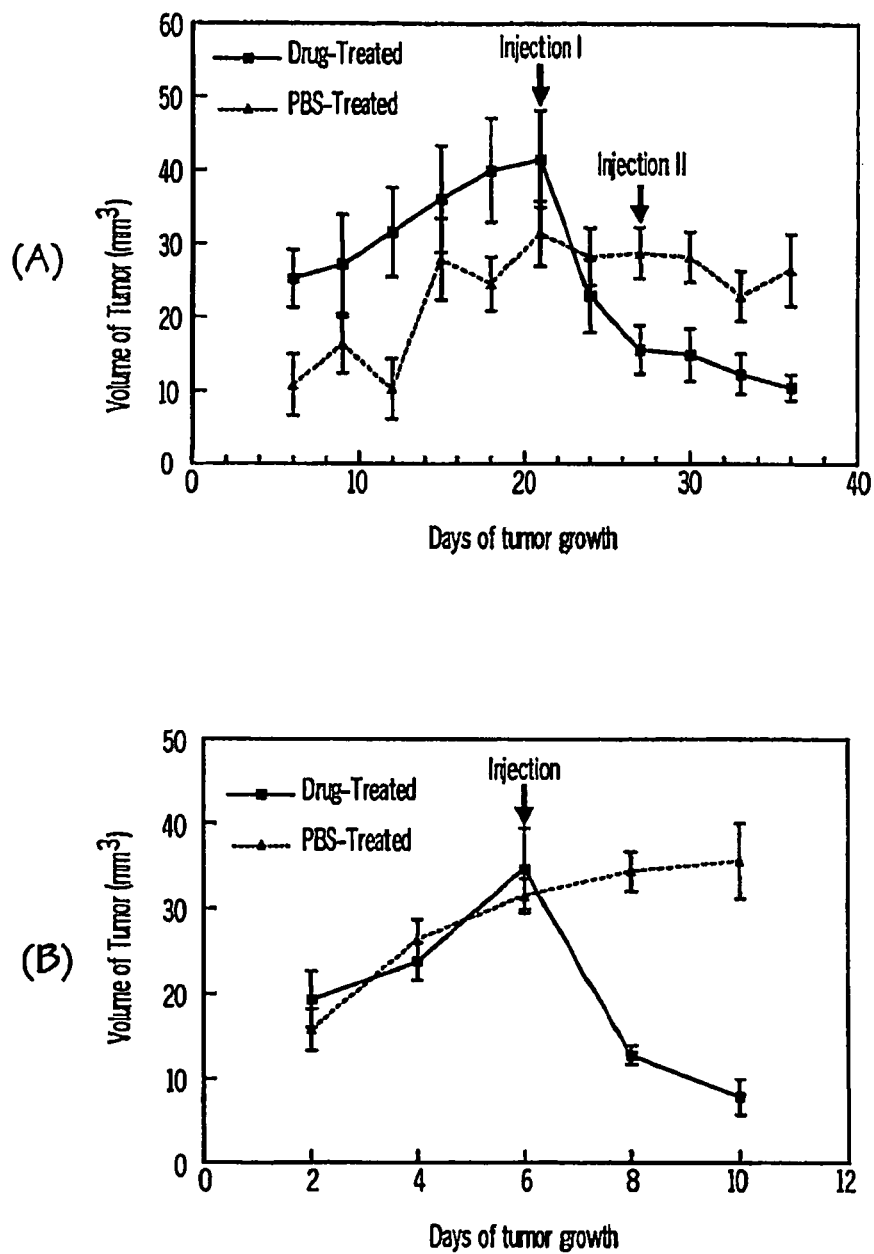
FIG. 3 presents results obtained from assessment of the average tumor volume on nude mice bearing human squamous cell carcinoma xenografts prior to and subsequent to subcutaneous injection of either a placebo (phosphate buffered saline, indicated with solid triangles and dashed lines) or agent of the invention (saposin C at 10 mg/Kg body weight/DOPS at 2 mg/Kg body weight, indicated with solid squares and lines). Error bars indicate the standard error. Tumor volume is indicated in $mm^3$, and time is indicated as days of tumor growth. Panel A presents results obtained from mice treated twice. The days of the first and second injections are indicated with arrows. Panel B presents results obtained from mice treated once. The injection day is indicated with an arrow. Details of the experiments are described elsewhere herein.

Nude mice were maintained in accord with the Cincinnati Children's Research Foundation guidelines governing the care of laboratory mice. Two groups of five nude mice were injected on the up-back with $2\times10^6$ SCCs subcutaneously to initiate tumor growth. Two tumors were established in each mouse. The tumors were allowed to establish for 21 days. On day 21 the animals received a subcutaneous injection at the tumor site of either the PBS diluent alone or an agent comprising saposin C (10 mg/kg body weight) and DOPS (2 mg/kg body weight). On day 27 the animals received a second subcutaneous injection at the tumor site of either the PBS diluent alone or an agent comprising saposin C (10 mg/kg body weight) and DOPS (2 mg/kg body weight). Tumor sizes were measured every other day with a caliper and volumes were estimated according to the formula $V=(\pi/4)LW^2$. Results obtained from one such experiment are presented in FIG. 3, panel A.

In a separate set of experiments, nude mice were maintained in accord with the Cincinnati Children's Research Foundation guidelines governing the care of laboratory mice. Two groups of five nude mice were injected on the up-back with $2\times10^6$ SCCs subcutaneously to initiate tumor growth. Two tumors were established in each mouse. The tumors were allowed to establish for 6 days. On day 6 the animals received a subcutaneous injection at the tumor site of either the PBS diluent alone or an agent comprising saposin C (10 mg/kg body weight) and DOPS (2 mg/kg body weight). Tumor sizes were measured every other day with a caliper and volumes were estimated according to the formula $V=(\pi/4)LW^2$. Results obtained from one such experiment are presented in FIG. 3, panel B.

Figure 4:
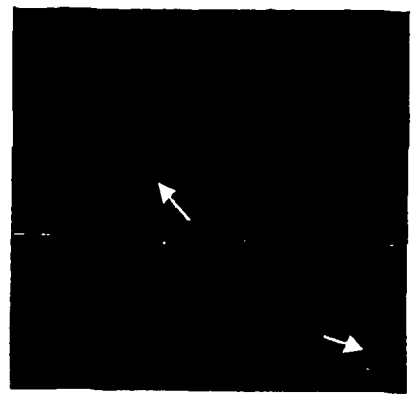
FIG. 4 presents fluorescent micrographs of human squamous cell carcinoma tumor tissues from xenografts. The cells in Panel A were treated with a fluorescently labeled mixture of phosphatidylserine and DOPS (NBD-DOSP/DOPS). The cells in Panel B were treated with a fluorescently labeled mixture of phosphatidylserine, DOPS, and saposin C. Details of the experiment are described elsewhere herein.
Figure 4:
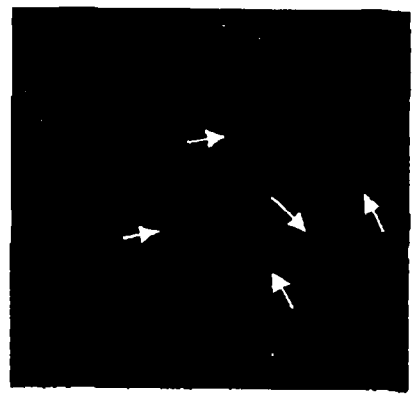

Example 7. Effect of Saposin C-DOPS on Human Squamous Cell Carcinoma Tumor Tissue Mouse xenografts were prepared with SCC tumors by methods known in the art. The fluorescent label nitrobenzoxadiazole (NBD) was linked to phosphatidylserine and a mixture of NBD-PS and DOPS was prepared. The NBD-DOPS was used to prepare a fluorescently labeled NBD-PS/DOPS/Saposin C complex. NBD-PS/DOPS was injected into the tumor at 0.1 mg NBD-PS/kg body weight and 2 mg DOPS/kg body weight. NBD-PS/DOPS/Saposin C was injected into the tumor at 0.1 mg NBD-PS/kg body weight, 2 mg DOPS/kg body weight, and 10 mg saposin C/kg body weight. Tumors were harvested 24 hours after administration of the agent. Microsections of the tumors were examined for fluorescence. Results from such an experiment are shown in FIG. 4.

Example 8. Ex Vivo Analysis of Saposin C-DOPS Effect on Human Cells

Cells from human cancer tissue and healthy tissue were grown in media suitable to the cell line. Cells from the following cancer tissue and healthy tissue cell lines were analyzed: Breast cancer: MCF-7, MCF-7 transfected with a dominant negative caspase 9, MCF-7 transfected with a vector control, BT-549; Head and neck: SCC-25, FaDu; Melanomas: MeWo, Sk-Mel-28; Leukemias: K-562, HL60; Cervical cancer: Hela; Ovarian cancer: PA1, PA1 transfected with a dominant negative caspase 9, PA1-E6; SK-OV3; Prostate cancer: DU145, PC3; Neuroblastomas: SK-N-SH, SK-SY-5Y, CHLA-79; Ewing sarcoma: 5838; T cell lymphomas; Rodu T; GCT; Lung cancer: A549, H441; Liver cancer: HepG2; Healthy breast: MCF-10A; and Healthy keratinocytes: NIK. 96-well flat-bottom tissue culture plates (Falcon, Becton-Dickson Labware, Franklin Lakes N.J.) were seeded with cells at a density of $10^4$ cells per well. Cells were plated in 100 tl complete medium with or without an agent of the invention.

The conversion of 3-(4,5-dimethylthiazol-2-yl)-2,5-diphenyltetrazolium bromide (available from Sigma) to a formazan product (18992) was used to assess viable cell density. Seventy-two hours after culturing the cells, 3-(4,5-dimethylthiazol-2-yl)-2,5-diphenyltetrazolium bromide (MTT) was added to each well to a final concentration of 0.25 mg/ml. The plates were incubated at 37° C. for 3 hours in the dark. The reactions were terminated by the addition of 0.04 N HCl in isopropanol. The plates were thoroughly mixed and analyzed at 570 nm on a micro ELISA plate reader (SpectraMax Plus, Molecular Devices, Sunnyvale Calif.). Growth curves and regression analysis were performed using PharmTools Pro computer software (The McCary Group, Elkins Park, Pa.).

| Human Cells | Cell Death (%) | | |
|---|---|---|---|
| Cancer Cell Lines | Non-treated | Treated | Known Gene Defects |
| Breast: MCF-7 | 6.8 ± 3.5 | 96.1 ± 1.0 | Caspase-3 null |
| MCF-7 (transfected) | 7.5 ± 3.5 | 18.9 ± 6.8 | Caspases-9 DN |
| MCF-7 (transfected) | 10.7 ± 3.7 | 94.0 ± 0.7 | Vector control |
| BT-549 | 6.9 ± 2.8 | 33.6 ± 6.6 | p53 mutation |
| Head & neck: SCC-25 | 7.4 ± 2.8 | 57.8 ± 4.6 | p53 null |
| FaDu | 14.6 ± 5.7 | 91.0 ± 0.2 | |
| Melanomas: MeWo | 8.3 ± 2.6 | 81.9 ± 5.4 | p53 mutation |
| SK-Mel-28 | 7.7 ± 3.2 | 76.2 ± 2.0 | Apaf-1 & p53 mutations |
| Leukemia: K-562 | 7.0 ± 2.8 | 58.0 ± 3.4 | Apaf-1 & p53 nulls |
| HL-60 | 21.2 ± 5.4 | 44.2 ± 3.6 | p53 null |
| Cervix: Hela | 3.8 ± 1.1 | 47.3 ± 4.4 | p53 mutation |
| Ovarian: PA1 | 7.1 ± 1.9 | 89.9 ± 0.2 | |
| PA1 (transfected) | 8.3 ± 3.0 | 54.1 ± 2.5 | Caspase-9 DN |
| PA1-E6 | 10.6 ± 3.9 | 71.2 ± 2.7 | p53 mutation |
| SK-OV3 | 11.8 ± 5.9 | 47.4 ± 12.1 | |
| Prostate DU145 | 4.0 ± 1.2 | 37.0 ± 2.8 | |
| PC3 | 9.0 ± 2.6 | 48.9 ± 16.8 | |
| Neuroblastomas: SK-N-SH | 12.4 ± 4.6 | 51.7 ± 19.1 | Caspase-8 mutation |
| SK-SY-5Y | 3.7 ± 0.6 | 68.0 ± 12.3 | Caspase-8 mutation |
| CHLA-79 | 3.6 ± 0.6 | 52.5 ± 6.5 | |
| Ewing sarcoma: 5838 | 12.8 ± 3.7 | 72.1 ± 3.9 | |
| T cell lymphomas | 12.1 ± 2.0 | 77.2 ± 5.8 | |
| Rodu T | 6.1 ± 2.9 | 22.2 ± 8.5 | |
| GCT | 3.4 ± 1.4 | 26.6 ± 1.4 | |
| Lung A549 | 5.0 ± 0.8 | 25.2 ± 13.7 | p53 mutation |
| H441 | 10.1 ± 4.0 | 25.4 ± 2.2 | p53 mutation |
| Liver: HepG2 | 9.4 ± 3.1 | 22.0 ± 10.2 | |
| Normal Cells | | | |
| Breast: MCF-10A | 12.8 ± 5.2 | 19.5 ± 5.9 | |
| Keratinocyte: NIK | 16.1 ± 8.4 | 18.2 ± 6.7 | |

Example 9. Evaluation of the Saposin C/DOPS $IC_{50}$

Mixtures of Saposin C and DOPS at molar ratios of 1:7, 1:3, and 1:10 were prepared. Polypeptides comprised of various fragments of the Saposin C protein were prepared as described previously (Wang et al. (2003) *Arch. Biochem. & Biophys.* 415:45-53, herein incorporated by reference in its entirety). The mutant Saposin C polypeptides are as follows: HNSC is comprised of amino acid residues 1-40; H1 is comprised of residues 4-20; and H-2 is comprised of amino acid residues 24-40.

Human SK-Mel-28 Melanoma cells were cultured on 96 well flat bottomed tissue culture plates. The cells were covered with media containing various concentrations of saposin C, DOPS, HNSC:DOPS (1:3), H-1:DOPS 1:3; H-2: DOPS 1:1; or a mixture of full length Saposin C:DOPS at 1:7, 1:3, or 1:10. Each treatment was administered to quadruplicate plates of SK-Mel-28 cells. Cell inhibition was analyzed using the MTT conversion assayed described elsewhere herein. The data were analyzed by fundamental linear regression using PharmTools Pro computer software (The McCary Group, Elkins Park, Pa.). Results are presented in Table 2.

TABLE 2

| Samples | SK-Mel-28 Melanomas IC$_{50}$ | |
|---|---|---|
| | Saposin C | DOPS |
| Saposin C: DOPS (1:7) | 19.5 ± 11.0 | 136.6 ± 78.0 |
| Saposin C: DOPS (1:3) | 99.8 ± 13.0 | 299.3 ± 39.0 |
| Saposin C: DOPS (1:10) | 81.3 ± 13.2 | 8134 ± 132.3 |
| Saposin C only | 786.0 ± 25.4 | |
| DOPS only | | 14193.4 ± 1886.0 |
| HNSC (saposin C(1-40)): DOPS (1:3) | 211 ± 32 | 633 ± 96.0 |
| H-1 (saposin C helix-1): DOPS (1:3) | 327 ± 36 | 981 ± 108.0 |
| 11-2 (saposin C helix-2): DOPS (1:3) | 243 ± 20 | 729 ± 60.0 |

Example 10. In Vivo Analysis of Saposin C-DOPS Effect on Tumor Cells

Nude mice were maintained in accord with the Cincinnati Children's Research Foundation guidelines governing the care of laboratory mice. Mice were injected on the up-back with 2×10$^6$ SCCs subcutaneously to initiate tumor growth. The tumors were allowed to establish. The animals were treated with either DOPS (2 mg/kg body weight) or an agent comprising saposin C (10 mg/kg body weight) and DOPS (2 mg/kg body weight). Forty-eight hours after administration of the treatment, the tumors were harvested.

Tissue sections were prepared from the tumors and examined using a variety of methods.

Figure 5:
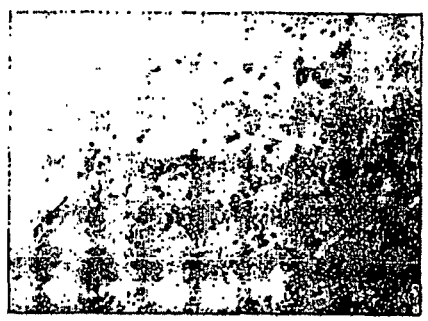
FIG. 5 presents micrographs of human squamous cell carcinoma tumor tissues from xenografts. Tissues were obtained from tumors treated with either DOPS (2 mg/kg of body weight, Panels A and C) or saposin C (10 mg/kg of body weight) and DOPS (2 mg/kg of body weight, Panels B and D). The tissues were stained with TUNEL staining (Panels A and B) or hematoxylin and eosin (Panels C and D). The arrows in Panel B indicate apoptotic cells. The dark staining in Panel D indicates area of necrosis.
Figure 5:
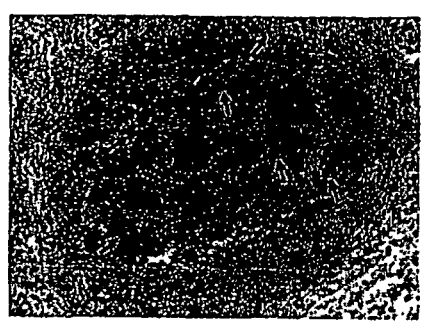
Figure 5:
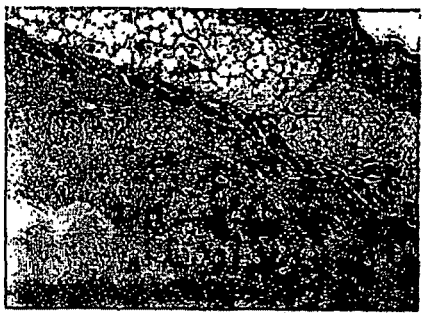
Figure 5:
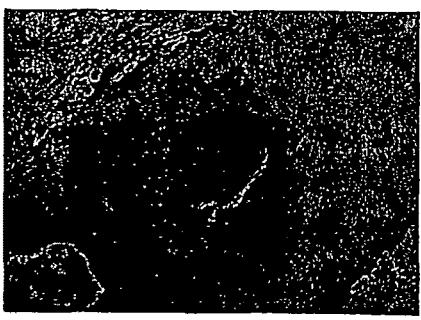

Tissue sections were examined by terminal deoxynucleotidyl transferase-mediated deoxyuridine triphosphate nick-end labeling (TUNEL) to evaluate apoptosis. (Results of one such experiment are shown in FIG. 5, Panels A and B.)

Tissue sections were stained with hematoxylin and eosin. (Results of one such experiment are shown in FIG. 5, Panels C and D.)

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for decreasing tumor volume in a subject comprising the step of administering to the subject a composition comprising
  a phospholipid, wherein the phospholipid is phosphatidylserine;
  an isolated saposin C-related polypeptide, wherein the polypeptide has an amino acid sequence at least 85 percent identical to SEQ ID NO: 2 and wherein the polypeptide includes amino acids 24-40 of SEQ ID NO:2; and
  wherein the phospholipid forms a nanovesicle incorporating the polypeptide.

2. The method of claim 1, wherein the composition further comprises a pharmaceutically acceptable carrier.

3. The method of claim 1, wherein the composition further comprises an additional active ingredient.

4. The method of claim 1, wherein the phosphatidylserine is selected from the group consisting of palmitoyloleoylphosphatidylserine, palmitelaidoyloleoylphosphatidylserine, myristoleoyloleoylphosphatidylserine, dilinoleoylphosphatidylserine, palmiticlinoleoylphosphatidylserine, lysophosphatidylserine, and dioleoylphosphatidylserine.

5. The method of claim 1, wherein the administration is selected from the group consisting of intravenous, parenteral, intradermal, subcutaneous, oral, transdermal, transmucosal, intraperitoneal, and rectal.

6. The method of claim 1, wherein the administration is given as a single dose.

7. The method of claim 1, wherein the administration is given as a multiple dose.

8. The method of claim 1, wherein the tumor is a brain tumor.

9. A method for treating a cancer in a subject comprising the step of administering to the subject a composition comprising
  a phospholipid, wherein the phospholipid is phosphatidylserine;
  an isolated saposin C-related polypeptide, wherein the polypeptide has an amino acid sequence at least 85 percent identical to SEQ ID NO: 2 and wherein the polypeptide includes amino acids 24-40 of SEQ ID NO:2; and
  wherein the phospholipid forms a nanovesicle incorporating the polypeptide.

10. The method of claim 9, wherein the composition further comprises a pharmaceutically acceptable carrier.

11. The method of claim 9, wherein the composition further comprises an additional active ingredient.

12. The method of claim 9, wherein the phosphatidylserine is selected from the group consisting of palmitoyloleoylphosphatidylserine, palmitelaidoyloleoylphosphatidylserine, myristoleoyloleoylphosphatidylserine, dilinoleoylphosphatidylserine, palmiticlinoleoylphosphatidylserine, lysophosphatidylserine, and dioleoylphosphatidylserine.

13. The method of claim 9, wherein the administration is selected from the group consisting of intravenous, parenteral, intradermal, subcutaneous, oral, transdermal, transmucosal, intraperitoneal, and rectal.

14. The method of claim 9, wherein the cancer is a brain cancer.

15. The method of claim 14, wherein the cancer is a glioblastoma.

16. The method of claim 1, wherein the nanovesicle has a diameter of between 10 nm and 1000 nm.

17. The method of claim 9, wherein a molar ratio of the polypeptide to the phospholipid is 1:1 to 1:50.

18. The method of claim 9, wherein the nanovesicle has a diameter of between 10 nm and 1000 nm.

19. The method of claim 8, wherein the brain tumor is a glioblastoma.

* * * * *